United States Patent [19]

Legrand et al.

[11] Patent Number: 5,082,940
[45] Date of Patent: Jan. 21, 1992

[54] PROCESS FOR THE PRODUCTION OF OXIDES OF AROMATIC TERTIARY AMINES

[75] Inventors: Franz Legrand, Quaregnon; Andre Lecloux, Meise; Paul Deschrijver, Asse-Zellik, all of Belgium

[73] Assignee: Interox (Societe Anonyme), Brussels, Belgium

[21] Appl. No.: 577,800

[22] Filed: Sep. 5, 1990

Related U.S. Application Data

[63] Continuation of Ser. No. 909,946, Sep. 22, 1986, abandoned.

Foreign Application Priority Data

Nov. 25, 1985 [FR] France .................... 85 17492

[51] Int. Cl.$^5$ ............... C07D 213/89; C07D 237/26; C07C 291/04
[52] U.S. Cl. ..................... 544/353; 546/348; 564/297; 564/298; 564/299
[58] Field of Search ............ 564/297, 298, 299; 544/353; 546/348

[56] References Cited

U.S. PATENT DOCUMENTS

| | | | |
|---|---|---|---|
| 3,047,579 | 7/1962 | Witman | 564/298 X |
| 3,390,182 | 6/1968 | Kollar et al. | 564/298 |
| 3,463,817 | 8/1969 | Mahnken | 564/298 |
| 3,776,959 | 12/1973 | Stalioraitis et al. | 564/298 |
| 4,504,666 | 3/1985 | Earl et al. | 564/298 X |

FOREIGN PATENT DOCUMENTS

| | | |
|---|---|---|
| 704364 | 4/1962 | Canada . |
| 687205 | 5/1986 | Canada . |
| 2099182 | 3/1972 | France . |
| 2265740 | 10/1975 | France . |
| 2076401 | 12/1981 | United Kingdom . |

OTHER PUBLICATIONS

E. Ochiai, Aromatic Amine Oxides, 1967.
C. C. J. Culvenor, Rev. Pure and Appl. Chem., 1953, pp. 83–114.
Kirk Othmer, Encyclopedia of Chemical Technology, 19, pp. 454–480.

*Primary Examiner*—Richard L. Raymond
*Attorney, Agent, or Firm*—Spencer & Frank

[57] ABSTRACT

Aromatic tertiary amines are oxidized by means of hydrogen peroxide in an inert solvent medium in the presence of a catalyst selected from metal selenium and compounds of selenium.

The process is applied to the preparation of oxides of heterocyclic aromatic tertiary amines and oxides of non-heterocyclic tertiary amines, in which the nitrogen atom is substituted by at least 1 aromatic nucleus.

9 Claims, No Drawings

PROCESS FOR THE PRODUCTION OF OXIDES OF AROMATIC TERTIARY AMINES

This application is a continuation of application Ser. No. 06/909,946, filed Sept. 22, 1986, now abandoned.

The present invention relates to a process for the production of oxides of aromatic tertiary amines according to which an aromatic tertiary amine is oxidised by means of hydrogen peroxide in a solvent medium and in the presence of a catalyst.

The products obtained by said process also come within the scope of the invention.

Tertiary amine oxides have been known for a long time and have numerous technical and biotechnical applications, particularly as intermediates in the synthesis of various organic compounds or as polymerisation inhibitors, preserving agents, antibiotics, pesticides, fungicides etc (Kirk Othmer—Encyclopedia of Chemical Technology—19—page 454-480; E. Ochiai—Aromatic Amine Oxides—1967).

It has been known for a long time that tertiary amine oxides can be produced by reaction of hydrogen peroxide with a tertiary amine in a solvent medium and that aromatic amines are less easy to oxidise than aliphatic amines, the oxidation problems being even greater than in the case of heterocyclic aromatic tertiary amines (pyridine, quinoline, picolines etc) and in the case of non-heterocyclic aromatic tertiary amines in which the nitrogen atom is substituted by at least 1 aromatic nucleus and by at least one other substituent having at least 3 carbon atoms (C. C. J. Culvenor—Rev. Pure and Appl. Chem., 1953, page 83-114). It has been established, for example, that dimethylaniline is readily oxidised by 3% hydrogen peroxide whilst methyldiphenylamine requires 30% hydrogen peroxide in acetic acid; similarly, alkylmethylaniline is hardly affected when it undergoes prolonged agitation in the presence of aqueous hydrogen peroxide (C. C. J. Culvenor—loc.-cit.—page 87). In order to overcome these problems, it was proposed that amine oxides be prepared by causing a tertiary amine to react with a peracid or with hydrogen peroxide in the presence of an acid such as glacial acetic acid, benzoic acid, phthalic acid etc in a solvent medium. These processes are time consuming, however, and require many operations before and after the synthesis, particularly during the separation stages of the end product which normally include evaporation, alkalisation and extraction. Moreover, organic peracids are very unstable and their use involves risks of explosion.

For all these reasons, other methods of oxidation were sought and a return was made to the use of hydrogen peroxide, in an inert medium, but in the presence of a catalyst chosen from the group composed of oxides, oxyacids and alkali metal salts of oxyacids of metals of the group composed of selenium, molybdenum, tungsten, vanadium and uranium (patent CA 704364) or of a catalyst based on an unstable inorganic percompound formed in situ from oxides, acids or acid salts of elements of groups VA, VI and VIII of the periodic table (patent CA 687205). In these two patents, the preferred catalysts are compounds of tungsten.

It has now been found that it is possible to improve the performance of the oxidation of aromatic tertiary amines by hydrogen peroxide, particularly a better degree of conversion of the amine and a lower hydrogen peroxide consumption if the catalyst is selected from selenium and compounds of selenium.

The present invention relates therefore to a process for the production of oxides of aromatic tertiary amines according to which an aromatic tertiary amine is oxidised by means of hydrogen peroxide in an inert solvent medium in the presence of a catalyst, characterised in that the catalyst is selected from selenium and compounds of selenium.

Although the invention is not confined to a particular type of aromatic tertiary amine, it is applied to advantage in cases where oxidation by hydrogen peroxide cannot take place readily without a catalyst, in particular the oxidation by hydrogen peroxide of heterocyclic aromatic tertiary amines or of non-heterocyclic amines in which the nitrogen atom is substituted by at least 1 aromatic nucleus and by at least one other substituent having at least 3 carbon atoms. Examples of such amines are pyridine, 2-picoline and 3-picoline, methylpropylphenylamine, diphenylmethylamine and allylmethylaniline.

The catalyst used can consist of metal selenium, selenium oxide, selenious acid or even selenic acid although this latter compound is less reactive and less selective than those cited above. It is also possible to use organic compounds of selenium, particularly organoselenium compounds. It has been established that the use of selenium oxide is particularly advantageous.

These catalysts are used preferably in concentrations of between 3.5 and 55 mmoles per mole of amine, preferably in the region of 30 to 40 mmoles per mole of amine. They can be added in the pure state, in solution or in dispersion.

An examination of the effect of the amine: hydrogen peroxide molar ratio has shown that the higher this ratio, the greater the selectivity towards amine oxide with respect to $H_2O_2$.

$$\frac{\text{number of moles of oxide formed}}{\text{number of moles of } H_2O_2 \text{ consumed}} \times 100,$$

the selectivity with respect to the amine consumed being virtually constant (approx. 100%). Amine:hydrogen peroxide molar ratios of between 0.8 and 2 are suitable. Molar ratios of between 1.1 and 1.8 are particularly suitable and result in only the amine having to be recycled. In practice, it is advisable to keep this molar ratio in the region of 1.25 so as to obviate the need to recycle an excessively large amount of amine.

In the process according to the invention, oxidation can be carried out in a liquid medium. It is generally advantageous for the liquid medium to be obtained by dissolution, in an inert solvent, of the aromatic tertiary amine, hydrogen peroxide, water and catalyst. It is not necessary for the catalyst to be completely in solution, its presence in dispersion in the liquid medium being sufficient. To this end, aliphatic alcohols such as ethanol, isopropanol and n-butanol, cyclohexanol, benzyl alcohol and, moreover, dioxane have proved to be effective solvents. n-Butanol is particularly suitable. On the other hand, alcohols with a dielectric constant of more than 26 (at 25° C.) such as methanol or butane diol and water give substantially inferior results. The use of polyethylene glycol can also be envisaged; it makes it easier to separate the catalyst with a view to recycling it.

As far as the quantity of solvent to be used is concerned, tests have shown that a dilution has a favourable effect on the degrees of conversion of hydrogen peroxide and the amine used $$\left( \text{degree of conversion of } X = \frac{\text{number of moles of } X \text{ consumed}}{\text{number of moles of } X \text{ used}} \times 100 \right)$$

and on the selectivity with respect to $H_2O_2$. However, it is not economic to use a large quantity of solvent and, moreover, the effect of dilution eventually reaches a constant level. The degree of dilution must therefore be examined beforehand as a function of the type of amine and solvent used. Generally, a solvent quantity of between 100 ml and 500 ml per mole of amine used is suitable. In the case of pyridine and n-butanol, for example, a volume of approximately 300 ml n-butanol per mole of pyridine is a good compromise.

The water contained in the reaction mixture may originate from the reagents (notably $H_2O_2$) or be formed by the reaction. Although it does not stop the reaction, it can be established that it has an adverse effect on the activity of the catalyst and on the selectivity of the reaction. It is advisable therefore to remove this water and, to this end, it is possible to use processes of evaporation such as distillation, azeotropic distillation or entrainment by means of an inert gas. It is also possible to fit the reactor with a florentine decanter to remove the water from the reflux liquid and to conduct tests under partial vacuum in order to ensure a correct reflux. The use of concentrated solutions of $H_2O_2$ is recommended (for example 70% $H_2O_2$ or above).

The temperature and the pressure at which the reaction is carried out can vary widely. A suitable operating temperature is in the region of 70° to 80° C. and it is possible to adjust the pressure so as to entrain the water at this temperature.

It is possible to add certain additives to the reaction mixture, for example stabilisers of hydrogen peroxide, polymerisation inhibitors or possibly inorganic or organic derivatives capable of fixing the water of the reaction mixture. These additives, if any, are generally present in a quantity of less than 3% of the weight of the reaction mixture.

The duration of the reaction depends on the type of amine to be oxidised and on the catalyst and solvent used. It can vary between 1 minute and 50 hours.

The process according to the invention can be used continuously or batchwise in a single reactor or in a series of reactors in parallel or in series. In order to carry out the process of the invention, it is possible to use any equipment suitable for liquid reaction mixtures.

The catalyst and the reagents can be introduced in various ways known in themselves. It is thus possible to carry out a single introduction, a continuous introduction or a step-wise introduction of the catalyst, aromatic amine and/or hydrogen peroxide.

A particular method of carrying out the process according to the invention consists in keeping the reaction mixture substantially water-free. In this case, the water concentration of the mixture is kept preferably below 2% of its weight. Very good results have been obtained when the reaction mixture contains less than 1% by weight water, for example between 0.05 and 0.9% by weight.

In order to keep the mixture in a substantially water-free state, any water that may be in it is removed continuously. To this end, various methods which have already been mentioned above can be used, namely processes of evaporation such as distillation, azeotropic distillation, entrainment by means of an inert gas and the use of a florentine decanter.

If the water forms with one of the constituents of the mixture such as the solvent a minimum azeotrope whose boiling point is lower than that of the constituents of the mixture and of any other azeotropes that might form, the water is generally removed by azeotropic distillation.

It is also possible to add to the reaction mixture at least 1 agent of azeotrope distillation of a different kind to that of the reaction solvent. This agent is chosen from those capable of forming, with water, a minimum azeotrope whose boiling point is lower than that of the other constituents of the mixture and of any other azeotropes that might form. It is chosen such that it is inert towards the other constituents of the mixture under the reaction conditions. Moreover, it is chosen in such a way that it does not disturb the homogeneity of the reaction mixture. Most often, it is chosen from chlorinated hydrocarbons and aromatic hydrocarbons. Chlorinated hydrocarbons containing 1–6 carbon atoms and aromatic hydrocarbons possibly substituted by alkyl groups or halogens and containing 6–12 carbon atoms are suitable. Good results have been obtained with methylene chloride, chloroform, 1,2-dichloroethane, 1,2-dichloropropane and benzene.

The entrainment agent is used in variable quantities, the amounts being chosen such as to maintain the homogeneity of the reaction mixture. Generally, it is used in quantities not exceeding 50% and most often 30% of the weight of the reaction mixture. When an agent of azeotropic distillation is used, it is employed in quantities of at least 1% in general and most often 3% of the weight of the reaction mixture.

This method can be used advantageously if the water does not form with the reaction solvent a minimum azeotrope whose boiling point is lower than that of the other constituents of the mixture and of any other azeotropes that might form.

The removal of water by azeotropic distillation is particularly suitable if the azeotrope thus formed is a heterogeneous azeotrope, because it is possible in this case to recycle the organic phase to the reaction mixture, after separation of the aqueous phase from the distillate. It is possible to separate the aqueous phase from the distillate by any methods known in themselves. Decanting methods are employed to advantage. The use of a florentine decanter is particularly suitable.

If the boiling point of water is lower than that of the other constituents of the reaction mixture and of any azeotropes that might form, a distillation process or a process of water entrainment by continuous passage of an inert gas into the reaction mixture is used most often. This latter method is generally used if it is desired to avoid bringing to boiling point those mixtures liable to decompose at their boiling point.

According to another particular way of carrying out the process according to the invention, the aromatic tertiary amine, in solution in the solvent, is allowed to react with hydrogen peroxide without continuous removal of the water present in the reaction mixture. In this case, the reaction mixture can advantageously be heated under reflux in order to remove the heat of reaction.

After reaction, the mixture can undergo various methods of separation such as distillation and decanting in order to collect the amine oxide and the unconverted reagents which can be recycled advantageously to the process.

The process according to the invention can be carried out continuously. To this end, the equipment described and illustrated in French patent FR-B-8112797 filed on the June 26, 1981 (INTEROX Société Anonyme) can be used to advantage.

In order to illustrate the invention yet without limiting its scope, some examples of production of aromatic amine oxides are given below (examples 1, 2, 3, 4, 5, 6 and 14). Examples 7R to 13R are given by way of comparison.

EXAMPLE 1

A quantity of 150 ml butanol, 45 ml (556 mmoles) pyridine and 2 g $SeO_2$ (18 mmoles) is introduced successively into a double jacket glass reactor heated by oil circulation and on top of which is situated a condenser kept at 290 K. The reaction mixture is raised to a temperature of 353 K. and 13 ml of 84% $H_2O_2$ (445 mmoles) are introduced in 10 minutes. After a total reaction time of 2 hours, the pyridine oxide is determined by vapour phase chromatography: 350 mmoles. The following results have therefore been obtained:

| | |
|---|---|
| Degree of conversion of the amine %, | 63 |
| Selectivity towards oxide with respect to the amine consumed %, | 100 |
| Degree of conversion of $H_2O_2$ %, | 91 |
| Selectivity towards oxide with respect to $H_2O_2$ consumed %, | 84. |

The excess amine and the catalyst can be recycled.

EXAMPLE 2

A quantity of 150 ml n-butanol, 45 ml (556 mmoles) pyridine and 2 g $SeO_2$ (18 mmoles) is introduced successively into a reactor similar to the one in example 1 but fitted with a florentine designed to collect the water removed from the reaction mixture by azeotropic distillation. The reaction mixture is raised to a temperature of 353 K. under a pressure of $2 \cdot 10^4$ Pa and 13 ml of 84% $H_2O_2$ (445 mmoles) are introduced in 10 minutes. After a total reaction time of 2 hours, the pyridine oxide is determined by vapour phase chromatography: 362 mmoles.

The results below were obtained:

| | |
|---|---|
| Degree of conversion of the amine %, | 65 |
| Selectivity towards oxide with respect to the amine consumed %, | 100 |
| Degree of conversion of $H_2O_2$ %, | 98 |
| Selectivity towards oxide with respect to $H_2O_2$ consumed %, | 83. |

The excess amine and the catalyst can be recycled.

EXAMPLES 3 and 4

The tests described in examples 1 and 2 are repeated, but this time using 70% hydrogen peroxide. Without distillation, the selectivity with respect to $H_2O_2$ consumed is 74% (degree of conversion 85%) and the degree of conversion of the amine is 56%. With distillation, on the other hand, the selectivity with respect to $H_2O_2$ consumed is 82% (degree of conversion 93%) and the degree of conversion of the amine is 62% (selectivity approx. 100%).

EXAMPLE 5

A quantity of 150 ml n-butanol, 45 ml 2-picoline (462 mmoles) and 2 g $SeO_2$ (18 mmoles) is introduced successively into a reactor similar to the one in example 2. The reaction mixture is raised to a temperature of 353 K. under a pressure of $2 \cdot 10^4$ Pa and 13 ml of 84% $H_2O_2$ (445 mmoles) are introduced in 10 minutes. After a total reaction time of 2 hours, the picoline oxide is determined by vapour phase chromatography: 357 mmoles. The results are as follows:

| | |
|---|---|
| Degree of conversion of the amine %, | 82 |
| Selectivity towards oxide with respect to the amine consumed %, | 96 |
| Degree of conversion of $H_2O_2$ %, | 91 |
| Selectivity towards oxide with respect to $H_2O_2$ consumed %, | 89. |

EXAMPLE 6

A quantity of 150 ml n-butanol, 45 ml 3-picoline (462 mmoles) and 2 g $SeO_2$ (18 mmoles) is introduced successively into a reactor similar to the one in example 2. The reaction mixture is raised to a temperature of 353K. under a pressure of $2 \cdot 10^4$ Pa and 13 ml of 84% $H_2O_2$ (445 mmoles) are introduced in 10 minutes. After a total reaction time of 2 hours, the picoline oxide is determined by vapour phase chromatography: 356 mmoles. The results are as follows:

| | |
|---|---|
| Degree of conversion of the amine %, | 78 |
| Selectivity towards oxide with respect to the amine consumed %, | 99 |
| Degree of conversion of $H_2O_2$ %, | 98 |
| Selectivity towards oxide with respect to $H_2O_2$ consumed %, | 82. |

EXAMPLE 7R

A test identical to the one in example 2 is carried out but replacing $SeO_2$ by 4.2 g tungsten oxide ($WO_3$) (18 mmoles). The pyridine oxide is determined by vapour phase chromatography. Only the following results are obtained:

| | |
|---|---|
| Degree of conversion of the amine %, | 19 |
| Selectivity towards oxide with respect to the amine consumed %, | 61 |
| Degree of conversion of $H_2O_2$ %, | 100 |
| Selectivity towards oxide with respect to $H_2O_2$ consumed %, | 15. |

The superiority of $SeO_2$ is clearly revealed.

EXAMPLES 8R to 13R

Tests the same as the one in example 2 are carried out but replacing $SeO_2$ by tungstic acid, $H_2WO_4$ in the proportions indicated. The following results are obtained:

| No. of test | H$_2$WO$_4$ used, mmoles | Pyridine oxide obtained, mmoles | Degree of conversion of the amine, % | Selectivity towards oxide with respect to the amine, % | Degree of conversion of H$_2$O$_2$, % | Selectivity towards oxide with respect to H$_2$O$_2$, % |
| --- | --- | --- | --- | --- | --- | --- |
| 8R  | 0,4  | 22  | 12 | 32 | 100 | 5  |
| 9R  | 0,8  | 74  | 21 | 63 | 100 | 17 |
| 10R | 1,6  | 155 | 37 | 75 | 96  | 36 |
| 11R | 3,2  | 177 | 41 | 78 | 100 | 41 |
| 12R | 4,8  | 160 | 42 | 69 | 100 | 37 |
| 13R | 18,0 | 116 | 42 | 50 | 100 | 27 |

Here again, the superiority of SeO$_2$ as catalyst is clearly illustrated.

EXAMPLE 14

A quantity of 40 ml n-butanol, 25 ml 96% quinoline i.e. 203 mmoles and 250 mg SeO$_2$ is introduced successively into a reactor with a capacity of 125 ml. 6 ml of 85% H$_2$O$_2$ are then added in 10 minutes (i.e. 200 mmoles), and the mixture is allowed to react for 2 hours at 343 K. whilst removing the water formed by azeotropic distillation. 140 mmoles of quinoline oxide are obtained in this way. The results are as follows:

| | |
| --- | --- |
| Degree of conversion of the amine %, | 69 |
| Selectivity towards oxide with respect to the amine consumed %, | 100 |
| Degree of conversion of H$_2$O$_2$ %, | 86 |
| Selectivity towards oxide with respect to H$_2$O$_2$ consumed %, | 81. |

EXAMPLE 15

A quantity of 50 ml n-butanol, 200 mg SeO$_2$ and 6.5 g quinoxaline (50 mmoles) is introduced successively into a reactor with a capacity of 250 ml fitted with a magnetic stirrer and a florentine decanter which allows the removal of water from the reaction mixture. 300 mmoles of 85 weight % H$_2$O$_2$ are then added in 30 minutes, at 343 K. and under reduced pressure which is adjusted so as to maintain a slight reflux in the florentine decanter. The reaction is then allowed to take place during 90 minutes.

The formed precipitate is then collected and whashed with n-butanol at 277 K. and petroleum ether. After drying, a precipitate of 4.0 g is weighted. The NMR analysis of the precipitate shows that it contains 88% of quinoxaline dioxide.

We claim:

1. A process for the production of oxides of heterocyclic tertiary amines, comprising:
    oxidizing a heterocyclic tertiary amine selected from the group consisting of pyridine, 2-picoline, 3-picoline, and quinoxaline by means of hydrogen peroxide, the amine:hydrogen peroxide molar ratio being kept between about 1.1 and 1.8, in an aliphatic alcohol solvent medium in the presence of a catalyst selected from the group consisting of selenium, selenium oxide, selenious acid, selenic acid, and an organo selenium compound.
2. A process according to claim 1, wherein the catalyst used consists of selenium oxide.
3. A process according to claim 1, wherein the catalyst is used in a quantity of between 30 and 40 millimoles per mole of amine.
4. A process according to claim 1, wherein the amine: hydrogen peroxide molar ration is kept about 1.25.
5. A process according to claim 1, wherein the reaction is carried out in an inert solvent medium composed of an aliphatic alcohol selected from ethanol, isopropanol, n-butanol and polyethylene glycol, of cyclohexanol, benzyl alcohol or dioxane.
6. A process according to claim 1, wherein the water introduced by the reagents or formed during the process is removed from the reaction mixture by an evaporation operation selected from distillation, azeotropic distillation or entrainment by means of an inert gas.
7. A process according to claim 1, wherein the reaction is carried out at a temperature of between 70° and 80° C. and in that the pressure is adjusted so as to entrain the water at this temperature.
8. A process according to claim 1, wherein at least 1 additive chosen from stabilisers of hydrogen peroxide, polymerisation inhibitors and inorganic or organic derivatives capable of fixing the water of the reaction mixture is added to the reaction mixture.
9. A process according to claim 1, wherein a weight of water of between 0.05 and 0.9% of the weight of the mixture is kept in the reaction mixture.

* * * * *